United States Patent [19]

Turner et al.

[11] Patent Number: 5,840,965
[45] Date of Patent: *Nov. 24, 1998

[54] PROCESS FOR THE PRODUCTION OF PURIFIED TELEPHTHALIC ACID

[75] Inventors: John Arthur Turner, Middlesbrough; Eric Hindmarsh, North Yorks; David Parker, Middlesbrough; Ian Peter Milne, Stockton-on-Tees, all of United Kingdom

[73] Assignee: E. I. du Pont de Nemours and Company, Wilmington, Del.

[ * ] Notice: The term of this patent shall not extend beyond the expiration date of Pat. No. 5,698,734.

[21] Appl. No.: 899,093

[22] Filed: Jul. 23, 1997

Related U.S. Application Data

[63] Continuation of Ser. No. 668,756, Jun. 24, 1996, Pat. No. 5,698,734.

[51] Int. Cl.$^6$ .................................................. C07C 51/43
[52] U.S. Cl. ........................................... 562/412; 562/414
[58] Field of Search ...................................... 562/412, 414

[56] References Cited

U.S. PATENT DOCUMENTS 3,452,088  6/1969  Olsen et al. .

*Primary Examiner*—Samuel Barts
*Attorney, Agent, or Firm*—Charles E. Krukiel

[57] ABSTRACT

Purified terephthalic acid is prepared by a process of subjecting an aqueous solution of crude terephthalic acid to hydrogenation to reduce impurities, crystallizing this solution to produce a slurry of purified terephthalic acid in an aqueous liquor, and carrying out an integrated separation washing process.

21 Claims, 6 Drawing Sheets

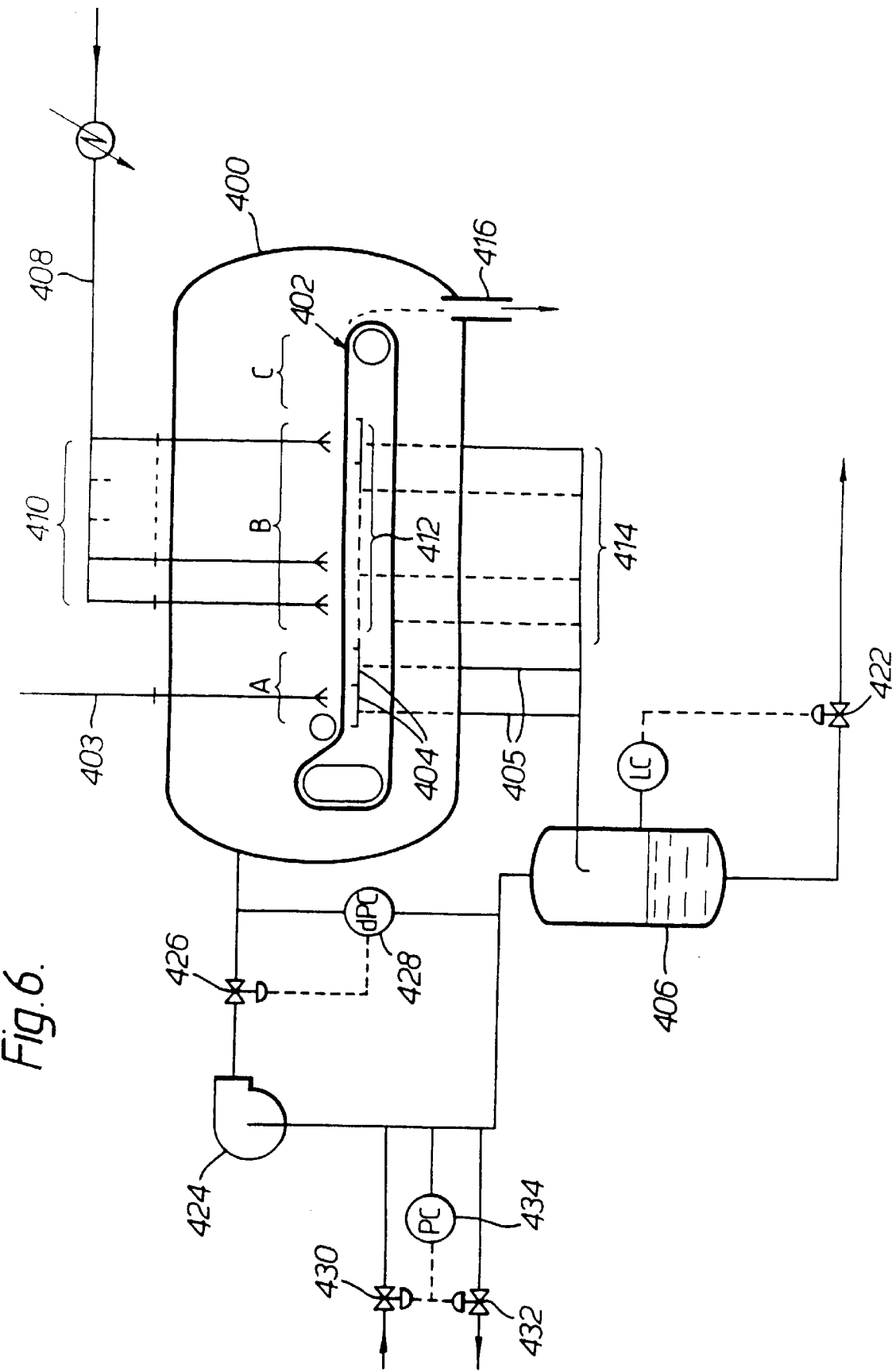

PROCESS FOR THE PRODUCTION OF PURIFIED TELEPHTHALIC ACID

This is a continuation, of application Ser. No. 08/668,756 filed on Jun. 24, 1996 now U.S. Pat. No. 5,698,734.

This invention relates to the production of terephthalic acid.

Purified terephthalic acid (PTA) is commonly produced by purification of crude terephthalic acid (CTA) obtained by the liquid phase air oxidation of p-xylene. It may also be produced by the hydrolysis of a polyalkylene terephthalate, for example polyethylene terephthalate.

Such purification typically comprises adding an aqueous medium to the CTA to form a slurry thereof which is then heated to dissolve the CTA in the medium to provide an aqueous solution of terephthalic acid. This solution is then passed to a reduction step in which the solution is contacted with hydrogen under reducing conditions in the presence of a heterogeneous catalyst to reduce chemically organic impurities, for example 4-carboxybenzaldehyde (4-CBA). The hydrogenated solution is passed to pressure let-down vessels in which PTA crystals form to provide a slurry of PTA in aqueous medium. PTA is recovered from the aqueous medium.

It is known to recover PTA from the aqueous medium by separating the PTA and medium in a decanter centrifuge in a first separation stage, reslurrying the PTA with fresh water, separating the reslurried PTA and fresh water in a decanter centrifuge in a second separation stage to produce a PTA cake and then drying the cake in a drier.

These steps involve special equipment which incur significant capital costs and variable costs of operation. The recovery stage requires large quantities of water in the centrifuge and reslurry steps. Therefore a large quantity of aqueous waste effluent must be treated and may present problems of disposal. Further, dissolved PTA and other valuable materials in the waste effluent stage may be lost.

The present invention seeks to provide improvements in the production of terephthalic acid.

According to one aspect of the present invention there is provided a process for the purification of crude terephthalic acid, comprising:

(a) dissolving the crude terephthalic acid in an aqueous medium to produce a terephthalic acid-containing solution;

(b) contacting the terephthalic acid solution with hydrogen under reducing conditions and at elevated temperature and pressure to reduce chemically at least some of the impurity present in the crude terephthalic acid;

(c) reducing pressure and temperature to obtain a slurry comprising crystallised pure terephthalic acid in aqueous medium;

(d) in a first zone effecting separation of the PTA crystals from the aqueous medium by filtration of the slurry to remove aqueous medium through a filter surface to obtain a wet mass of crystals;

(e) transferring said wet mass of crystals to a second zone without reslurrying said mass and supplying aqueous wash liquor to said mass while effecting filtration whereby the wash liquor is displaced through the mass and through a filter surface in the second zone; and (f) maintaining a differential pressure across the filter surface in at least one of said zones such that, on the lower pressure side of the filter surface, the pressure is substantially the same as or greater than the pressure prevailing following step (c).

Step (c) will normally be carried out in a series of crystalliser stages, in which the pressure and temperature is reduced progressively. Thus, the pressure differential of step (f) will therefore be such that, on the lower pressure side of the filter surface, the pressure is at least equal to the pressure prevailing in the final crystalliser stage, which will normally be superatmospheric, eg within the range 1.5 to 15 bars, more preferably 3 to 10 bars.

Preferably the pressure differential will be such that, on the lower side of the filter surface in each of said zones, the pressure is at least equal to the pressure prevailing following step (c).

Advantageously steps (d), (e) and (f) are carried out by discharging said slurry on to a filter material which is movable to transport the terephthalic acid through said first zone in which filtration of said aqueous medium from the slurry is effected, to the second zone in which said mass of crystals is washed by displacement of said aqueous wash liquor through said mass.

In this way, reslurry of the terephthalic acid is avoided and by effecting filtration through a filter surface in such a way that the lower pressure side of the filter surface is at a pressure no less than said superatmospheric pressure, liquid removal from the terephthalic acid can be effected substantially without accompanying flashing thereby reducing the tendency for soluble impurities to precipitate and contaminate the mass of purified terephthalic acid. In addition, any tendency for material to precipitate and foul the filter medium is reduced.

The filter material is suitably a metal gauze, or a cloth comprising a plastics material such as polyester, polypropylene, polyetheretherketone (PEEK) and the like. The filter surface is suitably in the form of a band, preferably a continuous band which is moved continuously or intermittently to convey material comprising terephthalic acid through the first and second zones.

The second zone may be followed by a third zone in which the washed deposit of PTA is removed from the filter surface by any suitable means, for example by scraping or by gravity.

Further, it is desirable to provide suitable means to pass liquid for example water or alkaline solution, through the returning part of the band to wash off downwardly facing adhering deposits into a receiver.

Usually the CTA employed in the production process of the invention is derived from the oxidation of paraxylene in a liquid reaction medium containing acetic acid to produce a slurry of CTA in the reaction medium. The liquid reaction medium normally incorporates a catalyst, for example a cobalt/manganese/bromide catalyst system which is soluble in the reaction medium. Suitably the oxidation is carried out in the presence of an oxygen source for example air, at a pressure of 5 to 30 bars absolute, and preferably an oxygen concentration of 0 to 8% by volume in the gas leaving the reactor and at a temperature of 150° to 250° C. It is suitably a continuous process, and is preferably carried out in a stirred reactor. The reaction is exothermic and the heat of the reaction may conveniently be removed by evaporation of water and acetic acid from the reaction medium.

The water and acetic acid evaporated from the reaction medium is preferably distilled to produce acetic acid having a lower water content. Acetic acid having a lower water content obtained in this way may be passed to the oxidation step and the water recovered from distillation may be used as the aqueous medium for dissolving CTA and/or as the aqueous wash liquor for washing PTA.

Following the oxidation step, the CTA produced may then be separated from the reaction medium conventionally by centrifugal separation and drying but it is more expedient to exchange the reaction medium, preferably continuously, for an aqueous medium to provide a terephthalic acid stream comprising CTA in aqueous medium in a process such as that disclosed in our prior co-pending EP-A-502628.

If desired, following combination of the CTA with aqueous medium to produce the terephthalic acid-containing solution, the resulting solution may be fed directly to the hydrogenation step or alternatively, may be treated prior to it being fed to the hydrogenation step. Such treatment may comprise subjecting the aqueous terephthalic acid-containing solution to oxidation to increase the conversion of terephthalic acid precursor compounds, especially 4-CBA, into terephthalic acid. Such oxidation may be effected in the aqueous phase using air or gaseous oxygen or a non-gaseous oxidising agent may be employed.

Suitably the heterogeneous catalyst employed in the purification of the crude terephthalic acid product is a supported noble metal catalyst, for example platinum, rhodium and/or preferably palladium on an inert, for example carbon, support. The reduction is suitably carried out by passing the terephthalic acid solution comprising terephthalic acid and impurities, for example 4-carboxybenzaldehyde, through a flooded bed of catalyst at a temperature of 250° to 350° C. in the presence of hydrogen. The solution suitably comprises 20 to 50% by weight of terephthalic acid.

The terephthalic acid solution, after reduction, is suitably cooled in a crystallisation process to a temperature in the range 100 to 220° C., typically 135° to 180° C., and a pressure of 3 to 10 bars, to produce solid purified terephthalic acid product.

Desirably, at least part of the aqueous medium removed in the first zone and at least part of the aqueous wash removed through the filter surface in the second zone is recovered and combined, directly or indirectly, with the CTA. The aqueous wash and/or medium thus desirably constitute at least a part of the aqueous medium with which the CTA is combined.

If both the aqueous medium and the aqueous wash are recycled, they may be mixed together to form a single stream prior to combination with the CTA. The aqueous medium and the aqueous wash may be treated, for example by distillation and/or evaporation to produce substantially pure water or at least partially eliminate para-toluic acid, either individually before mixing, or as a single stream after mixing prior to being combined with the CTA as desired.

Such treatment of the aqueous medium and/or wash may also comprise cooling, preferably to a temperature in the range 15° to 100° C., or evaporation of the aqueous medium and/or wash to produce a less pure precipitate and a residual mother liquor which are then suitably separated. Suitably, where the CTA is produced by an oxidation plant integrated with the purification plant, such less pure precipitate is returned to oxidation step of the oxidation plant. The mother liquor may be treated further and/or used as aqueous medium to be combined with the CTA.

The second zone desirably comprises a single stage wash in which the wash liquor passes through the filter surface only once either as a single stream or, following splitting of the wash liquor, as a plurality of streams. If desired the second zone may comprise a succession of wash stages wherein the wash liquid is passed through the filter surface more than once. The succession of wash stages may be co-current but is preferably counter-current in which, in each stage (other than the last), the incoming aqueous wash passed through the wet mass of crystals and the filter surface is the aqueous wash which has passed through the wet mass and the filter surface in the succeeding stage. In the last stage the aqueous wash liquor is preferably fresh incoming water.

The wash liquor is preferably introduced at a temperature which is substantially the same as the temperature of said mass as it enters the second zone so as to avoid problems with flashing or quenching (with the consequent risk of precipitating impurities).

The wash liquor is suitably at least in part water separated from acetic acid in the aforesaid distillation step following evaporation of acetic acid and water from the oxidation step, if present, or derived from other water streams within the process, for example from treatment of the aqueous wash and/or medium. This is advantageous as it reduces further the intake of fresh water and disposal of water in the process.

Typically the pressure differential across the filter surface in each of said zones is at least 0.05 bar with the side of the filter surface on which the mass of terephthalic acid crystals is located being at a higher pressure than the other side of the filter. Preferably the pressure differential is 0.1 to 10 bar, more preferably, 0.2 to 3 bar and especially 0.2 to 1 bar, for example 0.3 bar.

The actual pressure on the lower pressure side of the filter is maintained at such a pressure that the aqueous wash liquor in the second zone and, if applicable, the aqueous medium in the first zone which are removed through the filter surface, remain substantially in the liquid phase.

The higher pressure side of the filter surface is preferably maintained at elevated pressure, desirably at 2 to 15 bars and especially 3 to 10 bars and is desirably above the pressure of the preceding pressure-reducing step in the process.

The terephthalic acid slurry is suitably introduced into the first zone at a temperature of at least 60° C. and preferably 100° to 200° C., especially 120° to 180° C.

Suitably the slurry is deposited in such a way that the saturation pressure of the feed is less than the absolute pressure on the lower (downstream) side of the filter medium.

Deposition of the terephthalic acid stream at elevated temperature and pressure is advantageous as improved filtration is possible due to the aqueous medium being less viscous at elevated temperature. Furthermore there is less co-crystallisation of impurities for example p-toluic acid, with the terephthalic acid product at elevated temperature. Thus a higher purity terephthalic acid product is obtained and there is a correspondingly higher level of impurities for example p-toluic acid in the aqueous medium which is desirably recycled within the process. The elevated temperature may also permit heat recovery and hence provide a reduction in variable costs.

If recycle of aqueous medium and/or wash liquor is employed, it may be necessary to provide a purge to allow control of the level of components in the recycle stream.

According to a second aspect of the invention there is provided a process for the production of terephthalic acid comprising:

(a) effecting oxidation of paraxylene in a reaction medium comprising an aliphatic carboxylic acid to produce a first slurry of crude terephthalic acid in the reaction medium;

(b) subjecting said first slurry to a separation and washing process in which the reaction medium is removed from the crude terephthalic acid;

(c) dissolving the crude terephthalic acid from step (b) in an aqueous medium to produce a terephthalic acid-containing solution;

(d) contacting the terephthalic acid solution with hydrogen under reducing conditions and elevated temperature and pressure conditions to reduce chemically at least some of the impurity present in the crude terephthalic acid;

(e) reducing pressure and temperature to obtain a second slurry comprising crystallised purified terephthalic acid in aqueous medium containing reduced impurities in solution; and (f) subjecting the second slurry to a separation and washing process in which said aqueous medium is removed from the purified terephthalic acid with the aid of an aqueous wash liquor and without reslurrying the purified terephthalic acid prior to washing thereof with the aqueous wash liquor;

the separation and washing process carried out in each of steps (b) and (f) being implemented under elevated pressure conditions using a respective belt filter system.

Usually the second slurry will be at superatmospheric pressure following step (e).

The amount of water required in the process according to said second aspect of the invention is significantly reduced as compared with that required in prior art processes involving a reslurry operation. An important factor in this respect is the use of belt filters; such filters allow highly efficient washing to be carried out and because the separation of terephthalic acid from the reaction medium or aqueous medium can be integrated and carried out on the same filter belt, the need for reslurry of the terephthalic acid is eliminated. Overall therefore the amount of water employed in the terephthalic acid production process can be substantially reduced. In turn, the amount of waste effluent to be treated can also reduced substantially. Large quantities of effluent preclude the recycle of a substantial portion thereof into the terephthalic acid stream without further treatment. In said second aspect of the present invention a reduction in the amount of water required to provide a given wash efficiency allows liquid, herein referred to as mother liquor, recovered from the purification plant, for example aqueous medium from the separation of purified terephthalic acid product and the aqueous wash, to be recycled into the terephthalic production process. Such recycling is highly desirable as valuable materials in the mother liquor may be retained within the process rather than lost by disposal.

The improved washing efficiency allows higher impurity levels in the terephthalic acid stream to be tolerated. Consequently, the impurity level in the CTA which is fed to the hydrogenation step may be higher thus allowing beneficial re-optimisation of the process by which the CTA was produced, for example by reducing the severity of the oxidation reaction conditions. Further, the hydrogenation step and, if desired, the pressure and temperature reducing step may be also be re-optimised, if desired, such that the terephthalic acid stream has higher impurity levels.

According to a further aspect of the present invention, a process for the production of terephthalic acid comprises:

(a) effecting oxidation of paraxylene in a reaction medium comprising an aliphatic carboxylic acid to produce a first slurry of crude terephthalic acid in the reaction medium;

(b) subjecting said first slurry to an integrated separation and washing process in which the reaction medium is removed from the crude terephthalic acid and the crude terephthalic acid is washed with aqueous wash liquor;

(c) dissolving the crude terephthalic acid from step (b) in an aqueous medium to produce a terephthalic acid-containing solution;

(d) contacting the terephthalic acid solution with hydrogen under reducing conditions and elevated temperature and pressure conditions to reduce chemically at least some of the impurity present in the crude terephthalic acid;

(e) reducing pressure and temperature to obtain a second slurry comprising crystallised purified terephthalic acid in aqueous medium containing reduced impurities in solution;

(f) subjecting the second slurry to an integrated separation and washing process in which said aqueous medium is removed from the purified terephthalic acid and the purified terephthalic acid is washed with aqueous wash liquor;

(g) treating the aqueous medium removed in step (f) to produce a less pure precipitate of terephthalic acid and a residual aqueous mother liquor; and (h) recycling said less pure precipitate to the oxidation step (a) and/or recycling said residual mother liquor for use in step (c).

By "integrated separation and washing process" we mean that the separation and washing steps are carried out within the same item of equipment without an intermediate slurrying of the terephthalic acid in water prior to the washing step.

In one embodiment of said further aspect of the invention, the separation and washing process carried out in each of steps (b) and (f) is implemented under elevated pressure conditions using a respective belt filter system.

In another embodiment of said further aspect of the invention, the separation and washing process carried out in each of steps (b) and (f) may be implemented in the case of the separation stage in a first zone involving deposition of the terephthalic acid on a solid inner surface of a rotatable hollow vessel, for example a centrifuge, and in the case of the washing stage a filter surface forming a second zone of the vessel. The solid surface and the filter surface are suitably arranged such that the mass of purified terephthalic acid crystals is transported along the inner surface across the filter surface to a third zone, for example by a scroll on the inner wall of the hollow vessel, from which it is recovered and the aqueous medium from the terephthalic acid stream is transported away from the solid inner surface without crossing the filter surface as a result of the rotation of the hollow vessel, thereby effecting separation of the purified terephthalic acid and the aqueous medium. As the solid purified terephthalic acid passes over the filter surface, it is washed with an aqueous wash liquor which is removed through the filter surface to produce washed mass of terephthalic acid crystals. The washed mass is suitably transported to the third zone by rotation of the vessel and subsequently recovered from the third zone.

In practice, it is desirable to establish an atmosphere of inert gas over the filter cake in order to exclude or control the level of oxygen present. This inert gas also passes through the filter material in the washing zone and additional gas must be introduced in order to maintain the gaseous atmosphere. The inert gas may be nitrogen for instance, although in the case of the filter/washing system employed in the purification stage of the process, the inert gas may with advantage comprise steam.

Thus for instance the process of the invention as defined in any of the above aspects thereof preferably comprises means for supplying pressurised gas to the washing zone to establish a pressurised gaseous atmosphere on that side of filter surface on which the layer or mass or terephthalic acid crystals is formed. The gas from said atmosphere will be drawn through the mass of terephthalic acid crystals along with the wash liquor and preferably means is provided for recovering the gas and treating it to eliminate or at least reduce contamination thereof by the liquor, and the treated gas may be reintroduced into said atmosphere.

At least the separation step, and preferably the washing step also, is carried out in such a way as to prevent any substantial precipitation of solute from the liquid component. For instance, the liquor component in the purification stage may comprise a substantial content of solute in the form of paratoluic acid which should desirably be maintained in solution.

Thus, according to a preferred feature applicable to all of the aspects of the invention defined above, the pressure differential established between the upstream and downstream sides of the filter medium is created by means of a pressurised fluid constituted at least in part by a solvent component of the liquor, which component is in its vapour phase whereby flashing of the solvent component actually present in the liquor is substantially suppressed during filtration of the terephthalic acid/liquor slurry.

By employing a pressurised fluid based on the solvent component actually present in said liquor or said liquid, it is possible to conduct the filtration in such a way that the filter cake is not chilled or at least only cooled to a somewhat lesser extent than is the case where the pressurised fluid comprises nitrogen or other inert gas.

It is highly desirable that the partial pressure of said solvent component in or forming the pressurised fluid on the downstream side of the filter medium is maintained substantially at or above the vapour pressure of the solvent component actually present in the slurry fed to the upstream side of the filter medium.

The solvent component employed as said pressurised fluid may be derived from a product stream from which the liquor to be filtered is derived.

Thus, for instance where the process of the present invention is employed for the filtration of the product stream resulting from the liquid phase oxidation of para-xylene in acetic acid as solvent, filtration of the slurry may be effected using acetic acid vapour as the pressurised fluid. The acetic acid may, but need not necessarily, be derived from the acetic acid evaporated from the liquor during a crystallisation process (which may be conventional) carried out following withdrawal of the acetic acid/terephthalic acid slurry from the oxidation reactor. In this case therefore, following the crystallisation process in which further terephthalic acid crystallises out from the liquor, the slurry is passed to a filtration zone in which the method according to the invention is carried out using, as the pressurised fluid, acetic acid vapour derived from the crystallisation process.

Similarly where terephthalic acid (however obtained) is purified by dissolving the same in water and subjecting the solution to hydrogenation, the purified terephthalic acid is subsequently recovered by filtration using water vapour as the pressurised fluid, ie. in the form of steam. Again the steam may, but need not necessarily, be derived from a crystallisation process following the purification process.

The pressurised fluid may consist substantially wholly of said solvent component in the vapour phase but we do not exclude the possibility of incorporating in the pressurised fluid a non-condensible gas (usually one which is inert with respect to the liquor/crystals system,. eg nitrogen). By non-condensable, we mean a gas which is only condenses at temperatures somewhat below normal room temperature and pressure.

Where a mixture of the solvent component and a gas are employed, the composition should desirably be such that the partial pressure of the solvent component in the pressurised fluid is substantially at or above the vapour pressure of the solvent component in the slurry at the feed condition of the latter.

Usually the solvent component will comprise the major fraction (by volume) of said pressurised fluid.

Preferably the filtration is carried out in such a way that the temperature differential across the filter cake is essentially zero, and typically no more than 1° to 2° C.

Other more specific features of the process defined with reference to said first aspect of the invention are also optionally incorporated in said second and third aspects where the context admits. In some cases, for instance where the terephthalic acid-containing aqueous solution is subjected to an oxidation reaction prior to step (d) of said second or third aspect of the invention in order to oxidise terephthalic acid precursors such as 4-CBA to terephthalic acid, the lower pressure side of the filter may be at or below atmospheric pressure if desired.

BRIEF DESCRIPTION OF DRAWINGS

The invention will now be described by way of example only with reference to the accompanying drawings, in which:

FIG. 6 is a schematic diagram showing another form of filtration system in which pressurisation is effected by means of a solvent component present in the liquor.

Referring to FIG. 1, reactor A is fed with paraxylene and acetic acid containing a dissolved catalyst comprising cobalt, manganese and bromine ions by line 1 and with air via line 2. Product from the reactor A is passed to crystallisation section B by line 3. The temperature within the reactor A is controlled by evaporating a mixture of acetic acid and water from the reactor to a condensing system C via line 4 and is typically above 150° C. Most of the condensate is returned to the reactor A via line 5 with noncondensibles venting via line 6. To control the water content of the reactor A, part of the condensate is removed from the condensing system via line 7 and passed to the distillation column D.

Figure 1:
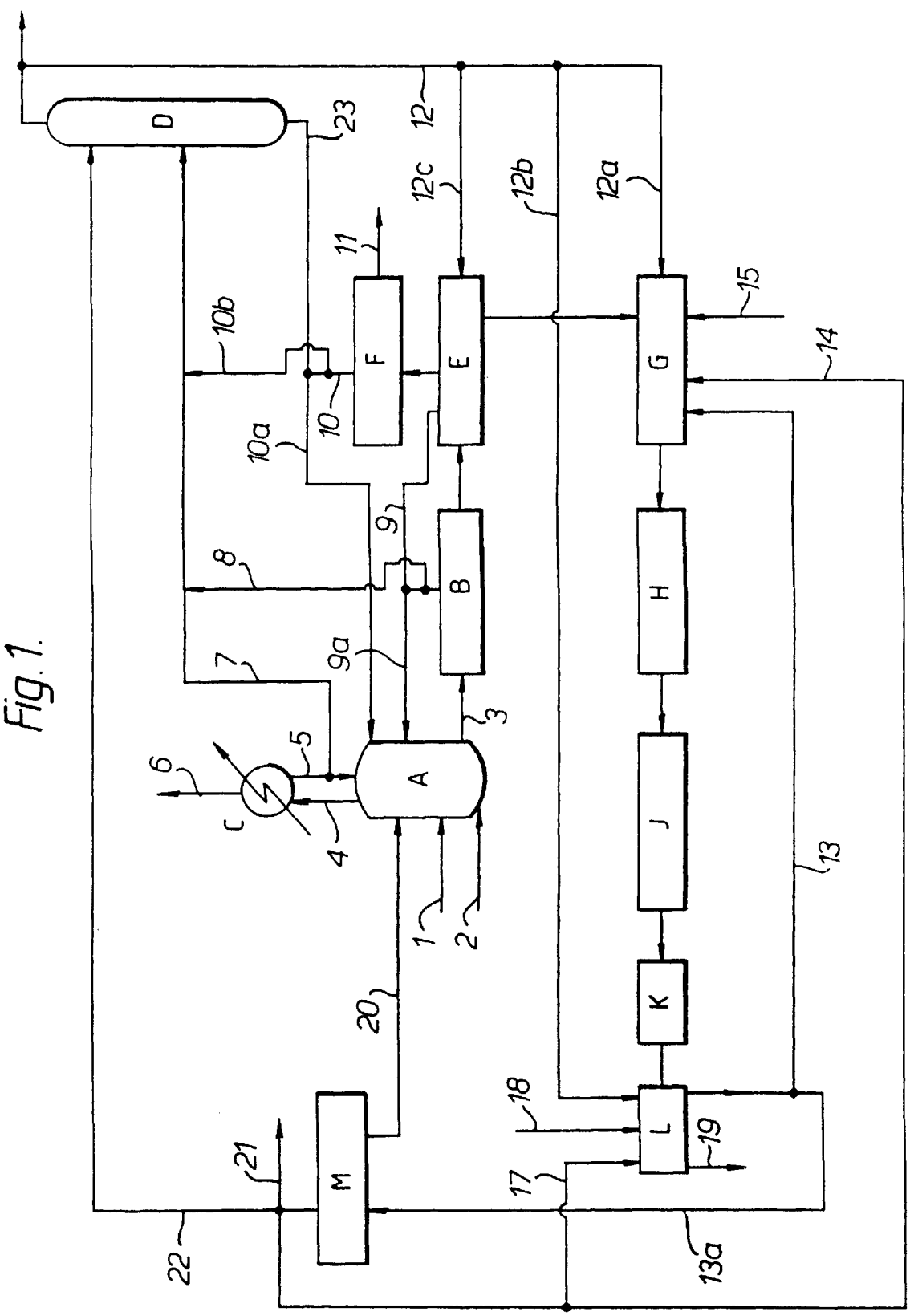
FIG. 1 is flow sheet of a terephthalic acid production process in accordance with the present invention.

In the crystallisation section B the temperature is dropped to approximately 80° C. to 150° C. and the slurry containing crystalline terephthalic acid in reaction mother liquor (mainly acetic acid) thereby produced is passed to a separation stage E. Acetic acid and/or water may be recovered from crystallisation section B and passed to the distillation column D via line 8 and/or to the reactor A via line 9a. The crystallisation section B typically comprises a series of crystalliser vessels in which the pressure and temperature of the slurry withdrawn from the oxidation reactor A is progressively reduced. In a typical embodiment of the invention, the resulting slurry of crude terephthalic acid in acetic acid-based mother liquor is reduced to a pressure in the range 0.5 to 2 bars and a temperature in the range of 90° to 130° C.

Separation stage E may be a conventional centrifuge and drier arrangement but is preferably an integrated separation and washing stage in which a continuous solvent exchange process is carried out, eg. as disclosed in our prior EP-A-502628. Reaction mother liquor recovered from stage E is returned in part via lines 9 and 9a to the reactor A optionally by first mixing with the fresh catalyst, paraxylene and acetic acid contained in line 1. Any remaining reaction mother liquor and any wash liquid is suitably passed to an evaporation stage F in which water and acetic acid vapour is removed by line 10, condensed and passed to reactor A via line 10a or optionally passed to distillation column D via line 10b. A purge of by-products and catalyst is withdrawn via stream 11.

The solids material, ie crude terephthalic acid (CTA), recovered from the separation stage E is transferred to reslurry stage G. In reslurry stage G, the CTA crystals are reslurried with water recovered from the distillation column D via lines 12, 12a and/or other water which may be recycle mother liquor via stream 13, recycle mother liquor via stream 14 and/or demineralised water via stream 15. The slurry produced in this stage is heated in section E to a temperature of for example 250° C. to 350° C. to form an aqueous solution of CTA which is passed to reactor J in which it is reacted with hydrogen over a fixed bed palladium catalyst thus reducing impurities in the solution and then crystallised in crystallisation section K. The temperature to which the solution is cooled in the crystallisation section K and the rapidity of cooling is adjusted to produce the appropriate purity of the desired terephthalic acid product. The crystallisation section K typically comprises a series of crystalliser vessels in which the pressure and temperature of the hydrogenated solution is progressively reduced. In a typical embodiment of the invention, the resulting slurry of purified terephthalic acid in aqueous mother liquor is reduced to a pressure in the range 3 to 10 bars and a temperature in the range of 135° to 180° C.

The slurry from the final stage of the crystallisation section K is transferred at the pressure and temperature prevailing in the final crystalliser stage to section L in which an integrated separation and washing process is carried out. Thus, in stage L, PTA crystals are separated from the aqueous mother liquor and the separated PTA product is washed with water which may be derived from column D via lines 12, 12b, recovery stage M via line 17 and/or fresh water via line 18 and is recovered, following washing, via line 19. The aqueous mother liquor from the separation in stage L is passed to recovery stage M via line 13a and/or to reslurry stage G via line 13.

In stage M the aqueous mother liquor is evaporated or further cooled so as to permit the recovery of further solids in the form of a less pure precipitate of terephthalic acid which is passed back to reactor A via stream 20. In stage M the temperature of the liquor may be reduced by flashing steam from it at, for example, atmospheric pressure. Such steam may be further purified for example by distillation in column D via line 22 and used if desired as wash in stage L, used elsewhere in the process or purged. The remaining liquor may be cooled or evaporated further and solids separated from it and recycled to reactor A via line 20 as desired.

The mother liquor recovered from stage M may be in part passed back to the distillation column D via line 22 and processed as described later, may be returned to the reslurry stage G via stream 14 and/or be purged via stream 21. Preferably, if the aqueous mother liquor is evaporated, the evaporated water is returned to the reslurry stage G via line 14.

The distillation column D fractionally distills a mixture of water and acetic acid evaporated from the reaction medium in condenser system C and is modified if required for use for the treatment of mother liquor separated from stages F and M. The column D comprises three zones; an upper zone comprising for example 5 theoretical stages, a middle zone comprising for example 45 theoretical stages and a lower zone comprising for example 5 theoretical stages. Part of the mixture of acetic acid and water evaporated derived from the reactor A is passed via stream 7 optionally together with stream 8 and/or 10b to between the middle and lower zones of the column D. Mother liquor from the precipitation of terephthalic acid may be passed into the column D between the upper and middle zones via stream 22. Acetic acid and heavy material are passed from the base of the column D via stream 23 to reactor A. Water is condensed in the condenser and may be re-used in the process via stream 12.

Figure 2:
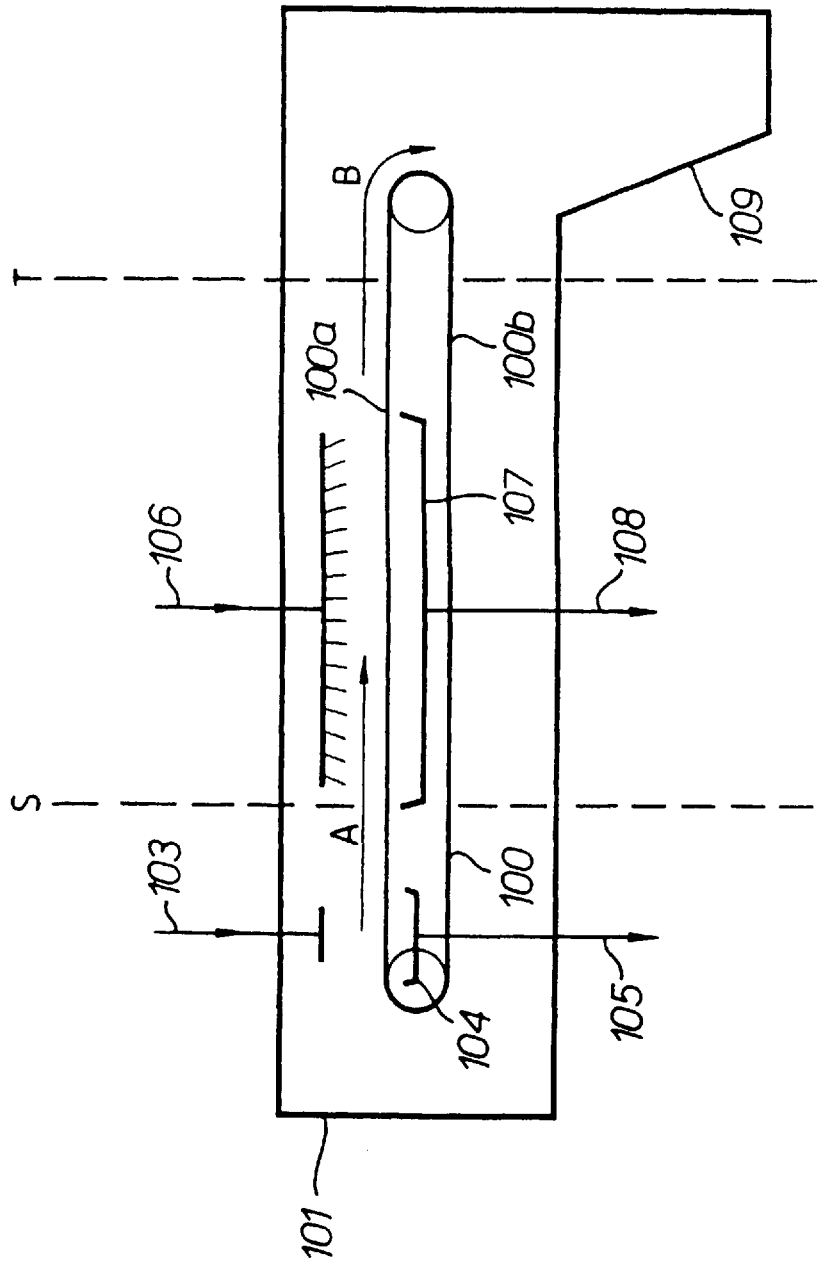
FIG. 2 is a schematic view of a belt filter system for use in the process of FIG. 1 and which integrates separation and washing stages.

Referring to FIG. 2, there is shown one embodiment for implementing an integrated separation and washing process suitable for use in each of stages E and L, in the form of a continuous band or belt filter unit such as a Pannevis filter of the form generally described in Filtration and Separation (Page 176 et seq, March/April 1979). The filter unit comprises an endless filter belt or band 100 driven by rollers around which the belt or band extends at each end, the belt being enclosed in a pressure tight housing 101. The belt 100 comprises generally horizontally disposed upper and lower runs 100a and 100b. The interior of the housing 101 is pressurised with a suitable gas such as nitrogen in the case of the filtration unit employed in stage E or nitrogen or steam in the case of the filtration unit employed in stage Dotted lines S and T show the locations of a first zone on the left, a second zone between the lines S and T and a third zone to the right of line T. The slurry of terephthalic acid in mother liquor (ie. acetic acid in the case of stage E or aqueous medium in the case of stage L) is introduced to the first zone via line 103 onto the band and mother liquor drains through the band into collector pan 104 from which it is removed via line 105 to leave a first wet deposit of terephthalic acid crystals which is then passed to a second (middle) zone (in the direction of arrow A). In the second zone, aqueous wash liquor, for example water, is introduced via line 106 and passed through the band to collector pan 107 to produce a second wet deposit. The aqueous wash is removed via line 108. The second wet deposit then passes to a third zone (in the direction of arrow B) in which it is removed from the band, collected in a receiver 109, recovered and then slurried with aqueous medium in the case of CTA or dried in the case of PTA.

The water introduced via line 106 may be derived from line 12b, 17 and/or 18 (stage L) or line 12c (stage E) as shown in FIG. 1 or any other suitable source. Suction is applied to the filter cake formed on the upper run 100a via the pans 104 and 107 and the pans are coupled together for reciprocating movement as a unit in a direction parallel to the direction of travel of the belt. During travel of the pans from left to right, suction is applied to draw liquid through the upper run 100a and during return travel of the pans, suction is terminated. The pressure differential across the filter belt, between the region above the filter cake and the downstream side of the filter medium (ie. the interior of the pans) is typically of the order of 0.6 bar. In the case of stage L, the pressure residing on the downstream side of the filter medium is at least as great as that prevailing in the final stage of the crystallisation section E. The wash liquor applied to the filter cake passes through the cake by virtue of the pressure differential between the upstream side of the filter cake and the downstream side of the filter medium and is applied in such a way that the wash liquor displaces residual mother liquor within the cake without undergoing channelling. It will be appreciated that the wash liquor may be applied in a single stage or it may comprise a series of stages with wash liquor applied at a number of locations along the path of travel of the filter belt. In this event, the wash liquor may be applied as a number of parallel streams or it may be applied in a serial manner, either co-current or counter-current. The mother liquor and wash liquor recovered from each filter belt unit are utilised in the manner described with reference to FIG. 1. Thus, for example, in the case of the filtration unit forming stage L, the mother liquor and recovered wash liquor may be combined and then subjected to cooling or evaporation to produce a less pure terephthalic acid precipitate which is recycled to the reactor A. The residual mother liquor/wash liquor may be further processed for example to reduce the para-toluic acid content thereof and then recycled to the reslurry stage G for use in dissolution of CTA prior to the hydrogenation reaction in reactor J.

The stages E and L may be implemented by other forms of filtration unit capable of operating under pressure; for instance, the filtration units may be constituted by pressure drum filters, eg multi-cell pressure drum filters of the type well-known in the filtration art or rotary cylindrical filters such as the type disclosed in EP-A-406424. Alternatively the integrated separation and washing units forming stages E and L may take other forms such as those described below.

Figure 3:
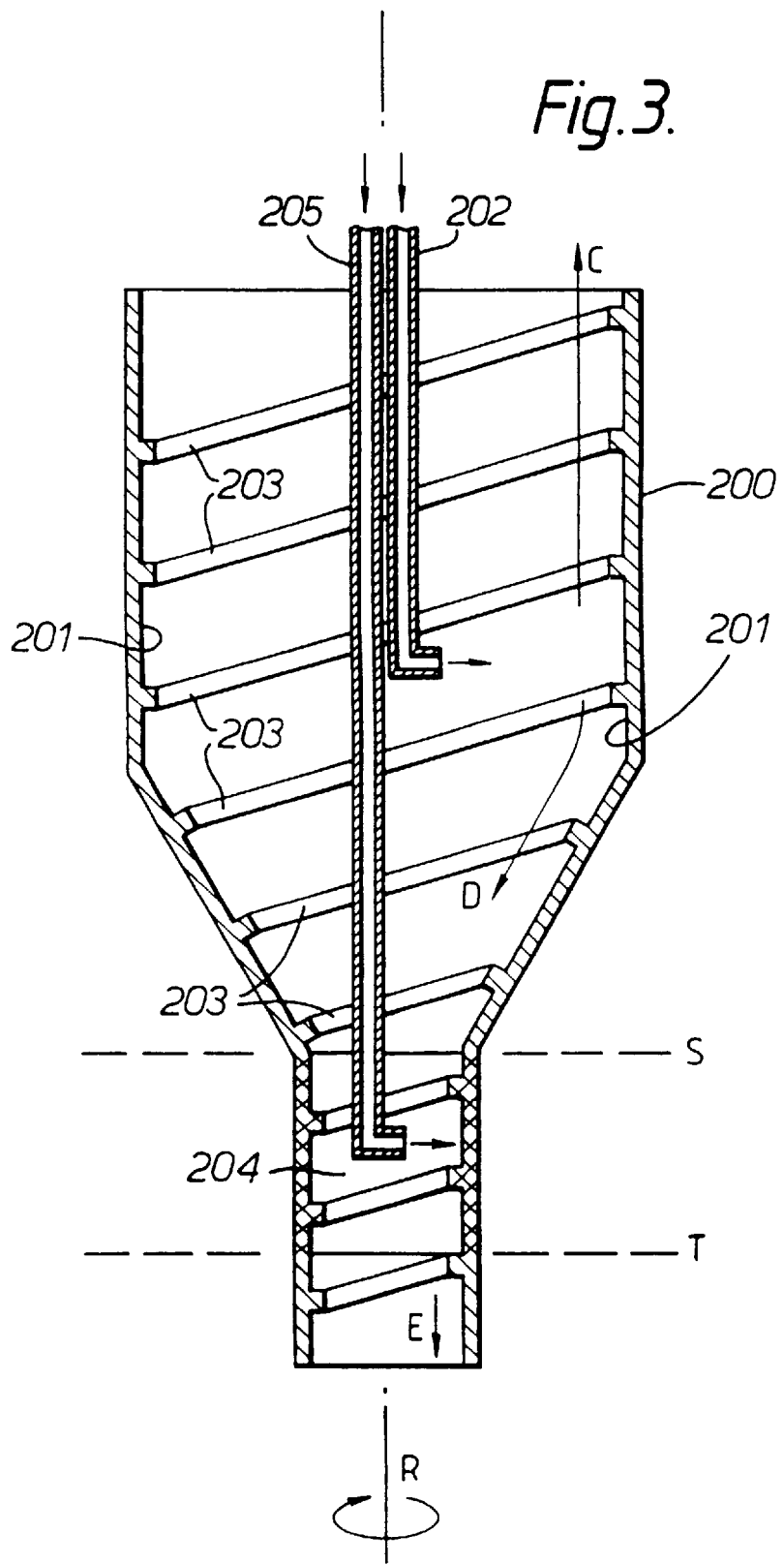
FIG. 3 is a diagrammatic cross-sectional view of one form of centrifuge for implementing integrating separation and washing stages.

FIG. 3 shows a cross-section representation of a centrifuge adapted for use in the present invention which comprises a hollow vessel 200 of circular cross section which is rotatable about its longitudinal axis R and which comprises an inner solid wall 201 onto which the terephthalic acid stream comprising terephthalic acid in an aqueous medium is deposited via inlet 202. Dotted lines S and T denote the boundaries between the zones, the first zone being above line S, the second zone being between lines S and T and the third zone being below line T. Rotation of the vessel causes a substantial proportion of the mother liquor component of the terephthalic acid slurry to be transported in the direction of arrow C, out of the first zone whilst the purified terephthalic acid-containing wet deposit is transported in the direction of arrows D, across the second zone and across the third zone by means of an inner scroll 203. In the second zone, the wet deposit passes across filter surface 204 and is washed with an aqueous wash liquor supplied by inlet 205. The aqueous wash liquor may be derived from sources such as those described in relation to the embodiment of FIG. 2. The wash liquor is withdrawn through the filter surface 204 and the wet deposit is retained by the filter 204 to produce a second wet deposit comprising terephthalic acid which is transported to the third zone in the direction of arrow E. The second wet deposit is then desirably removed from the third zone and processed further, ie by slurrying in stage G or drying depending on whether the terephthalic acid is in its crude or purified form.

Figure 4:
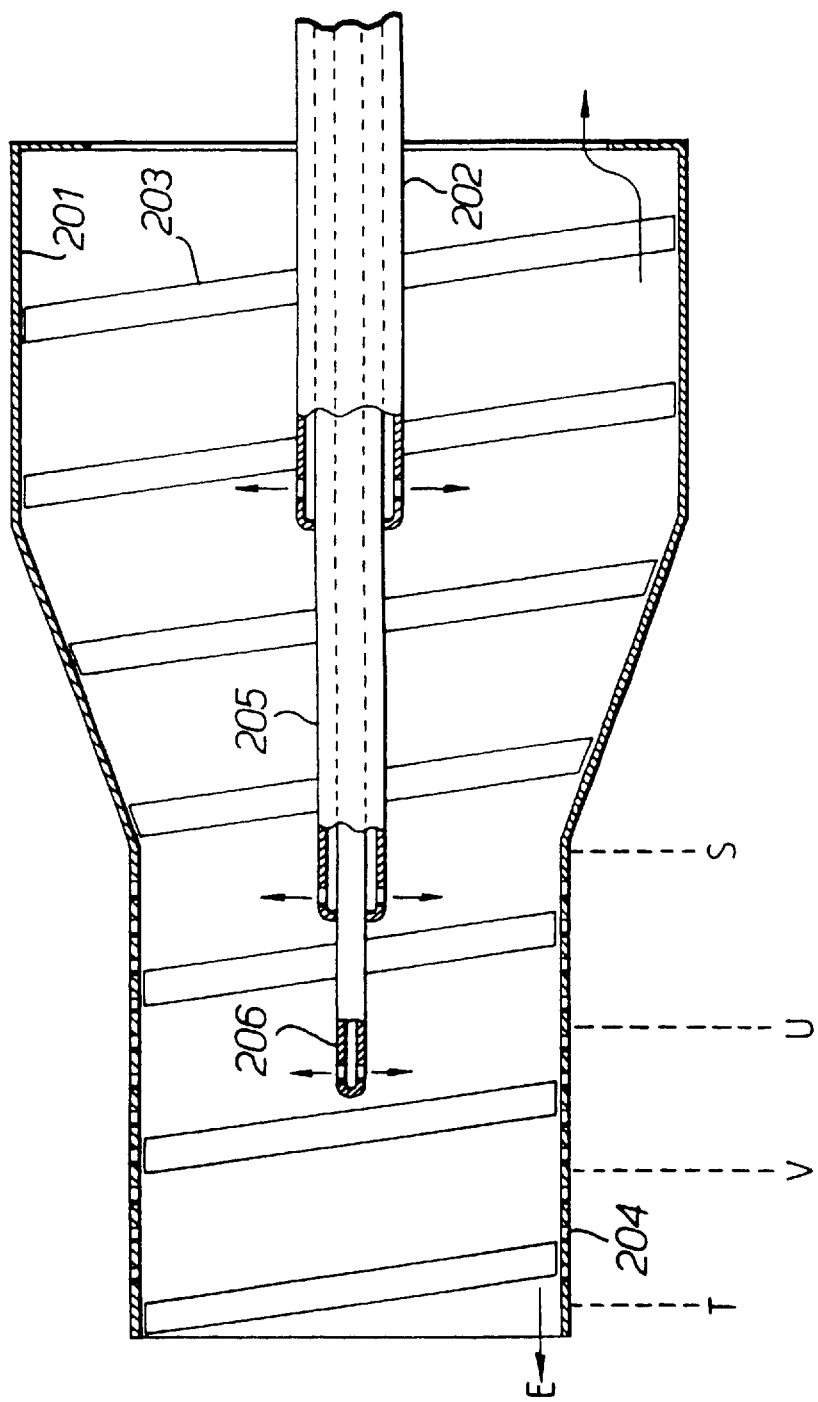
FIG. 4 is a diagrammatic view of an alternative form of centrifuge for use in a process in accordance with the invention.

FIG. 4 shows a cross section representation of another form of centrifuge adapted for use in the present invention, the same reference numerals being used in FIGS. 3 and 4 to depict like components. The centrifuge of FIG. 4 differs from that of FIG. 3 in several respects. Inlets 202 for depositing the terphthalic acid stream and inlet 205 for providing the aqueous wash are coaxially arranged along the longitudinal axis of the centrifuge and an additional aqueous wash inlet 206 is provided which is also coaxial with inlets 202 and 205. Inlet 202 has a greater diameter than inlet 205 which, in turn, has a greater diameter than inlet 206. A further difference between FIGS. 3 and 4 is that the second zone (between S and T) is sub-divided into a dewatering zone between V and T, and into two wash sub-zones between U and V, and S and U respectively. As the wet deposit of terephthalic acid is transported across the filter surface 204 in the sub zone between S and U, it is washed with aqueous wash via inlet 205 which wash has been obtained as the filtrate recovered from the succeeding sub-zone between U and V. As the deposit passes through the sub zone between U and V, it is washed with aqueous wash, preferably demineralised water, via inlet 206. Thus, the wet deposit is washed counter-currently as it passes through the part of the second zone. In the sub zone between V and T, the washed wet deposit may be dewatered by removing aqueous wash through the filter surface 204 to produce a second wet deposit which is then passed to the third zone in the direction of arrow E.

As the separation and washing processes are carried out under pressure somewhat in excess of atmospheric pressure, where it is desired to transfer the washed terephthalic acid to equipment operating at lower pressure (eg at atmospheric pressure), this may be effected either by reslurrying the filter cake or by transferring the filter cake in its moist condition from higher pressure to lower pressure using a suitable pressure isolating arrangement. For instance, a PTA filter cake removed from the filtration unit of FIG. 2 into the receiver 109 may be transferred to drying equipment at lower pressure by means of various devices such as variable pitch screws, the use of two lock vessels, one of which can be under pressure and filled with filter cake and the other open to atmosphere, or a rotary valve arrangement.

Figure 5:
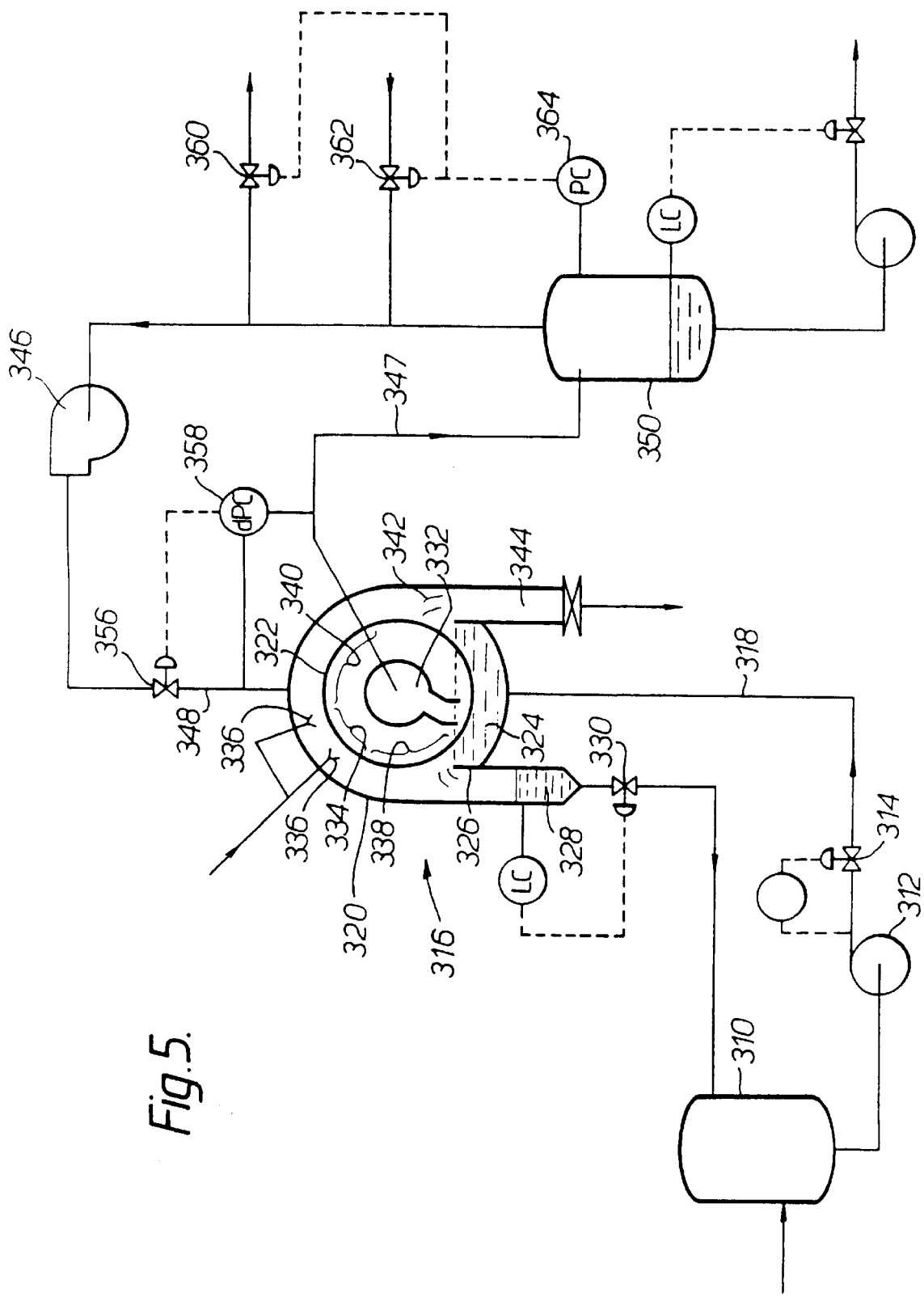
FIG. 5 is a schematic diagram showing one form of filtration system in which pressurisation on the upstream side of the filter medium is effected by means of a solvent component forming part of the liquor in which terephthalic acid is slurried.

Referring now to FIG. 5, this illustrates the use of a pressurising fluid for the filtration step in such a way as to reduce further any tendency for solute present in the slurry liquor to precipitate out and hence contaminate the terephthalic acid. As shown, slurry stored in a tank 310 is fed by pump 312 and flow controlled valve 314 to a rotary drum type filter 316 which may be of conventional design. The slurry is fed to the tank 310 via line 318 and may be derived for example from a crystalliser system (not shown) associated with plant for effecting purification of terephthalic acid by contacting an aqueous solution thereof with hydrogen in the manner previously described. The rotary vacuum filter 316 comprises an outer housing 320 within which a cylindrical support 322 carrying a filter medium (typically a filter cloth) is mounted for rotation about a horizontal axis perpendicular to the plane of the paper. The slurry is supplied to the lower region of the housing 320 which forms a reservoir 324 bordered on one side by weir 326 so that the slurry contained within the reservoir 324 is of constant depth. Overflow passes into section 328 from which it is withdrawn and recirculated via level controlled valve 330 to the slurry holding tank 310, the control being effected in dependence on the level of the slurry within section 328. Usually the slurry feed to the filter will be under pressure and at a relatively high temperature; for instance, typical pressure and temperatures of the slurry at the inlet to the rotary vacuum filter are about 8 bars and 170° C.

A suction unit 332 is located within the interior of the support 322 so as to exhaust fluid (both pressurising fluid and filtrate) from the interior of the filter medium. The arrangement is such that, as the support 322 rotates in a clockwise direction as viewed in FIG. 5, successive parts of the periphery of the cylindrical filter dip into the reservoir 324 and slurry is drawn against the filter medium. As the filter medium rotates, the applied suction serves to draw the liquor through the filter medium, forming a cake of solid material (eg crystals of terephthalic acid) on the upstream face of the filter medium. The filtration process is driven by the application of differential pressure across the filter medium. This pressure is developed by the supply of pressurised fluid to the space between the housing 320 and the filter medium. The pressure exerted by the fluid is such that a small pressure differential is established through the thickness of the filter cake. Typically, this pressure differential is of the order of 0.1 to 2 bar. With reference to the typical slurry pressure quoted above, the pressurised fluid may be supplied at a pressure of the order of 8.5 bars and the pressure at the downstream side of the filter medium is typically of 0.1 to 2 bar less but at least substantially the same as or greater than the pressure prevailing in the final stage of the crystallisation process.

At a location above the reservoir 324, the filter medium traverses a washing zone 334 in which with a washing medium such as water issuing from nozzles 336 is applied to the filter cake. In the (clockwise) direction of filter travel, this washing zone is preceded by a filtration zone 338 and is succeeded by a further filtration zone 340 in which the wash liquid and any residual liquor from the slurry is removed from the filter cake. The filter cake is then finally dislodged from the filter medium in the zone 342 by unshown means and falls into a collection section 344 from which it is recovered and optionally dried to produce substantially dry pure terephthalic acid.

The fluid used to pressurise the upstream side of the filter medium is constituted by the solvent component present in the liquor, ie water where the slurry is derived from the purification of terephthalic acid, the solvent used for the purpose of establishing the pressure differential being in its vapour phase. Thus, for example, steam pressurised by compressor 346 is introduced into the housing 320 via line 348 and circulates around a path in which it passes through the filter cake and the filter medium, enters suction unit 332 (along with filtrate), and returns to the compressor 346 via line 347 and line 352. Filtrate removed by suction unit 332 collects in the tank 350 from which it is withdrawn for further processing via level controlled valve 354. The supply of steam to the rotary filter is controlled by valve 356 and pressure differential sensor 358 coupled between lines 347 and 348. Excess steam may be purged, as necessary, from the system via valve 360 while make-up steam may be supplied, as necessary, via valve 362 both under the control of pressure sensor 364. The steam supply to the system may be derived from any suitable source; for instance, it may be constituted by steam derived from the purification process at a point upstream of the filtration system, a convenient source being steam produced during a conventional crystallisation process applied to the liquor withdrawn from the hydrogenation reactor.

The steam employed as the pressurising fluid will usually be at a temperature slightly above that at which the liquor is introduced into the filter. Thus, for example, where the liquor is introduced at a pressure of 8 bars and at 170° C., the steam admitted as the pressurising steam will be at about 173° to 175° C. and, in particular, at a temperature which ensures that there is no tendency for condensation. The arrangement is such that the temperature of the pressurising fluid on the upstream and downstream sides of the filter cake are substantially the same and the equipment will be thermally insulated to avoid heat losses as the pressurising fluid circulates around the system. In practice, the compression of the circulating fluid by compressor 346 introduces heat into the circulating steam and means may be provided for moderating or controlling the temperature of the steam entering the filter. For instance, this may be achieved by passing the steam through a heat exchanger following compression or by controlled injection of further steam or water (depending on whether heating or cooling is required) into the recirculating vapour to adjust the temperature thereof so that the steam entering the filter is within a desired temperature range.

Referring now to FIG. 6, there is shown schematically a filtration system in which a housing 400 encloses a continuous filter belt or band 402 which is driven so that the upper run thereof travels from left to right as viewed in FIG. 6. The upper run of the filter band 402 traverses three zones A, B and C. A slurry of terephthalic acid in aqueous liquor is introduced to the first zone via line 403 onto the band and aqueous liquor passes through the band 402 with the assistance of pressurised fluid, namely steam (which may be derived from the crystallisation section K or from elsewhere), the steam serving to develop a pressure differential between the space above the upper run of the band 402 and the space immediately beneath the upper run thereof. The aqueous liquor passing through the band 402 in zone A is collected in collector pans 404 located beneath the upper run of the band 402 and is removed from the pans 404 via lines 405 to leave a first wet deposit which is then passed to the second zone B. The aqueous liquor is fed via lines 405 to a filtrate pot 406.

In the zone B, aqueous wash, for example water, is introduced via line 408 and a series of sprays 410 and passes, with the assistance of the pressurised steam, through the band 402 to collector pans 412 to produce a second wet deposit. The aqueous wash is removed via lines 414 and fed to the filtrate pot 406. The second wet deposit then passes to zone C in which it is removed from the upper run of the band 402, collected at point 416, recovered and then optionally dried to produce substantially dry purified terephthalic acid. The water collecting in filtrate pot 406 is removed via line 420 and level controlled valve 422 for further processing as described above in relation to stage L of FIG. 1.

Although all of the liquor collected following filtration is shown as being collected in a common collection vessel, ie filtrate pot 406, it will be appreciated that liquor collected at different locations along the filter medium may be collected and supplied to different collection points as required. Also, as previously mentioned, the liquor collected at a location adjacent the end of the travel path of the upper run may, instead of being routed to the filtrate pot 406, be used to wash the deposit at a location preceding it, and likewise the liquor collected from the latter location may be used to effect washing at the location preceding it, and so on.

The pressurised steam is circulated around a loop including compressor 424, valve 426 (controlled by differential pressure sensor 428), the steam passing from the upstream side of the band 402 through the filter cake and the filter medium to the (downstream side) underside of the upper run of the band from where it passes to the filtrate pot 406 along with the filtered aqueous medium. Make-up steam is added to the system as needed, and steam is purged from the system when necessary, by means of valves 430, 432 controlled by pressure sensor 434. In an alternative embodiment, purge and make-up of the steam for pressurising the system may be effected by means of a balance line connected to the crystalliser from which the slurry is obtained. In this case, the need for valves 430 and 432 and sensor 434 is obviated. As described in relation to the embodiment of FIG. 5, the arrangement is such that temperature of the steam is substantially the same on each side of the filter cake and, where necessary, the temperature of the steam entering the filter may be moderated or controlled as previously described.

The filter system shown in FIG. 6 may be generally in the form of a belt filter of the type which is manufactured by Pannevis BV of Utrecht, Holland and uses intermittent application of vacuum as described for instance in the Proceedings of the Filtration Society, Filtration & Separation, March/April 1979, Page 176 et seq.

In carrying out the filtration process as described above in relation to the embodiments of FIGS. 5 and 6, the temperature at the upstream and downstream sides of the filter is maintained substantially the same, ie. isothermal operation, so as to substantially prevent the development of a supersaturation condition during the filtering operation, thereby preventing deposition of otherwise soluble constituents of the liquor and hence reduction in product quality and/or clogging of the filter medium.

We claim:

1. A process for the purification of crude terephthalic acid, comprising:
   (a) dissolving the crude terephthalic acid in an aqueous medium to produce a terephthalic acid-containing solution;
   (b) contacting the terephthalic acid solution with hydrogen under reducing conditions and at elevated temperature and pressure to reduce chemically at least some of the impurity present in the crude terephthalic acid;
   (c) reducing pressure and temperature to obtain a slurry comprising crystallised purified terephthalic acid in aqueous medium;
   (d) in a first zone effecting separation of the purified crystals from the aqueous medium by filtration of the slurry to remove aqueous medium to obtain a wet mass of purified crystals;
   (e) transferring said wet mass of crystals to a second zone without reslurrying said mass and supplying aqueous wash liquor to said mass while effecting filtration whereby the wash liquor is displaced through the mass in the second zone; and
   (f) recovering the aqueous medium from step (d) and/or the aqueous wash liquor from step (e) and recycling the same in the process whereby the water content thereof and valuable materials herein are retained within the process.

2. A process as claimed in claim 1 in which aqueous medium from step (d) and/or wash liquor from step (e) is recycled for use in step (a).

3. A process as claimed in claim 1 including treating said recovered aqueous medium and/or wash liquor before recycle within the process to reduce the paratoluic acid content thereof.

4. A process as claimed in claim 1 including treating said recovered aqueous medium and/or wash liquor before recycle within the process to produce substantially pure water.

5. A process as claimed in claim 3 in which said treatment comprises distillation.

6. A process as claimed in claim 4 in which said treatment comprises distillation.

7. A process as claimed in claim 5 in which the distillation is carried out in a column for use in the separation of water from acetic acid.

8. A process as claimed in claim 1 in which the washing operation of step (e) is carried out in a number of stages.

9. A process as claimed in claim 1 in which the washing operation of step (e) is carried out in a number of stages in counter-current fashion such that the terephthalic acid is contacted with aqueous wash liquor of increasing purity as it is progressed through the washing operation.

10. A process as claimed in claim 1 in which the filtration of steps (d) and (e) is carried out while conveying material comprising terephthalic acid on a band through said first and second zones.

11. A process as claimed in claim 10 in which the band is continuous.

12. A process as claimed in claim 1 including carrying out the filtration of steps (d) and (e) under elevated temperature and pressure to reduce the extent of co-crystallisation of paratoluic acid with terephthalic acid.

13. A process as claimed in claim 1 in which the slurry of terephthalic acid crystals introduced into the first zone is at a temperature in excess of 120° C. and up to 180° C.

14. A process as claimed in claim 1 in which the slurry of terephthalic acid crystals introduced into the first zone is at a temperature in the range of 170° C. to 200° C.

15. A process as claimed in claim 1 in which the slurry of terephthalic acid crystals introduced into the first zone is at a temperature in the range of 170° C. to 180° C.

16. A process as claimed in any claim 1 in which the filtration of steps (d) and (e) is carried out under a pressure of 2 to 15 bars on the slurry side of the filter material.

17. A process as claimed in claim 1 in which the filtration of steps (d) and (e) is carried out under a pressure of 8 to 15 bars on the slurry side of the filter material.

18. A process as claimed in claim 16 in which aqueous medium separated in step (d) is evaporated or cooled to produce a less pure terephthalic acid precipitate for recycle to said liquid phase oxidation of paraxylene.

19. A process as claimed in claim 1 in which the separation and washing of steps (d) and (e) are implemented under elevated pressure conditions using a filter system selected from the group consisting of a pressurised belt filter and a pressurised rotary cylindrical filter.

20. A process as claimed in claim 1 in which the separation and washing of steps (d) and (e) are implemented by means of a centrifuge provided with means for effecting washing of the terephthalic acid.

21. A process for the purification of crude terephthalic acid, comprising:
   (a) dissolving the crude terephthalic acid in an aqueous medium to produce a terephthalic acid-containing solution;
   (b) contacting the terephthalic acid solution with hydrogen under reducing conditions and at elevated temperature and pressure to reduce chemically at least some of the impurity present in the crude terephthalic acid;
   (c) reducing pressure and temperature to obtain a slurry comprising crystallised purified terephthalic acid in aqueous medium;
   (d) in a first zone effecting separation of the purified crystals from the aqueous medium by filtration of the slurry to remove aqueous medium to obtain a wet mass of purified crystals;
   (e) transferring said wet mass of crystals to a second zone without reslurrying said mass and supplying aqueous wash liquor to said mass while effecting filtration whereby the wash liquor is displaced through the mass in the second zone; and (f) recovering the aqueous medium from step (d) and/or the aqueous wash liquor from step (e) and treating the same whereby water and valuable materials therefrom are recovered for re-use in the process, such treatment being effected at least in part by means of a distillation column associated with an oxidation reactor for producing the crude terephthalic acid by the liquid phase oxidation of p-xylene in an acetic acid-based solvent, said distillation column being operable to separate from said acetic acid solvent water generated in the course of said liquid phase oxidation.

* * * * *